US010640737B2

(12) United States Patent
Lant et al.

(10) Patent No.: US 10,640,737 B2
(45) Date of Patent: May 5, 2020

(54) CLEANING COMPOSITION

(71) Applicant: The Procter & Gamble Company, Cincinnati, OH (US)

(72) Inventors: Neil Joseph Lant, Newcastle upon Tyne (GB); Jean-Luc Philippe Bettiol, Etterbeek (BE); Denis Alfred Gonzales, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/591,676

(22) Filed: May 10, 2017

(65) Prior Publication Data
US 2017/0327774 A1 Nov. 16, 2017

(30) Foreign Application Priority Data

May 10, 2016 (EP) .................................. 16169027

(51) Int. Cl.
| | |
|---|---|
| *C11D 3/38* | (2006.01) |
| *C07K 14/37* | (2006.01) |
| *C11D 3/00* | (2006.01) |
| *C11D 1/83* | (2006.01) |
| *C11D 1/94* | (2006.01) |
| *C11D 3/04* | (2006.01) |
| *C11D 3/30* | (2006.01) |
| *C11D 3/33* | (2006.01) |
| *C11D 3/386* | (2006.01) |
| *C11D 11/00* | (2006.01) |
| *C11D 1/14* | (2006.01) |
| *C11D 1/22* | (2006.01) |
| *C11D 1/29* | (2006.01) |
| *C11D 1/75* | (2006.01) |
| *C11D 1/90* | (2006.01) |

(52) U.S. Cl.
CPC .............. *C11D 3/38* (2013.01); *C07K 14/37* (2013.01); *C11D 1/83* (2013.01); *C11D 1/94* (2013.01); *C11D 3/0094* (2013.01); *C11D 3/046* (2013.01); *C11D 3/30* (2013.01); *C11D 3/33* (2013.01); *C11D 3/386* (2013.01); *C11D 3/38627* (2013.01); *C11D 3/38636* (2013.01); *C11D 3/38645* (2013.01); *C11D 11/0023* (2013.01); *C11D 1/143* (2013.01); *C11D 1/146* (2013.01); *C11D 1/22* (2013.01); *C11D 1/29* (2013.01); *C11D 1/75* (2013.01); *C11D 1/90* (2013.01)

(58) Field of Classification Search
CPC .................. C11D 3/38; C07K 14/37
See application file for complete search history.

(56) References Cited

U.S. PATENT DOCUMENTS

| | | | | | |
|---|---|---|---|---|---|
| 3,898,186 | A | * | 8/1975 | Mermelstein | C11D 1/75 510/108 |
| 5,230,823 | A | * | 7/1993 | Wise | C11D 10/04 510/235 |
| 5,376,310 | A | * | 12/1994 | Cripe | C11D 1/06 510/108 |
| 5,378,409 | A | * | 1/1995 | Ofosu-Asante | C11D 1/06 510/108 |
| 5,883,062 | A | * | 3/1999 | Addison | C11D 1/83 510/218 |
| 5,998,347 | A | * | 12/1999 | D'Ambrogio | C11D 1/83 510/237 |
| 2004/0234952 | A1 | * | 11/2004 | Kallow | C12Q 1/04 435/5 |
| 2009/0101167 | A1 | * | 4/2009 | Boeckh | C11D 3/0036 134/6 |
| 2009/0136433 | A1 | * | 5/2009 | Subkowski | A61K 8/64 424/59 |
| 2009/0305930 | A1 | * | 12/2009 | Becker | C11D 3/38 510/163 |
| 2013/0123160 | A1 | * | 5/2013 | Dobrawa | C11D 17/0017 510/221 |
| 2014/0031272 | A1 | | 1/2014 | Shipovskov | |
| 2014/0323380 | A1 | * | 10/2014 | Tajmamet | C11D 3/48 510/235 |

FOREIGN PATENT DOCUMENTS

| | | | |
|---|---|---|---|
| WO | WO9963034 A1 | 12/1999 | |
| WO | WO0071658 A1 | 11/2000 | |
| WO | WO 2010/034708 * | 4/2010 | ............ C12N 15/62 |
| WO | WO2013113556 A2 | 8/2013 | |

OTHER PUBLICATIONS

Case CM4478 Search Report; PCT/US2017/031708; dated Jul. 24, 2017; 17 Pages.
Kyte and Doolittle, J. Mol. Biol., 1982, 157, 105-132.
Wessels, Adv. Microbial Physiol. 1997, 38, 1-45.
Wosten, Annu. Rev. Microbiol. 2001, 55, 625646.

* cited by examiner

*Primary Examiner* — Amber D Steele
(74) *Attorney, Agent, or Firm* — Melissa G. Krasovec

(57) ABSTRACT

A cleaning composition including a) from about 1% to about 60% by weight of the composition of a surfactant system comprising an anionic surfactant and a primary co-surfactant selected from the group consisting of amphoteric surfactant, zwitterionic surfactant and mixtures thereof; and b) from about 0.001% to about 5% by weight of the composition of a class II hydrophobin.

17 Claims, No Drawings
Specification includes a Sequence Listing.

SEQUENCE LISTING

```
<160> NUMBER OF SEQ ID NOS: 1

<210> SEQ ID NO 1
<211> LENGTH: 71
<212> TYPE: PRT
<213> ORGANISM: Trichoderma reesei

<400> SEQUENCE: 1

Ala Val Cys Pro Thr Gly Leu Phe Ser Asn Pro Leu Cys Cys Ala Thr
1               5                   10                  15

Asn Val Leu Asp Leu Ile Gly Val Asp Cys Lys Thr Pro Thr Ile Ala
            20                  25                  30

Val Asp Thr Gly Ala Ile Phe Gln Ala His Cys Ala Ser Lys Gly Ser
        35                  40                  45

Lys Pro Leu Cys Cys Val Ala Pro Val Ala Asp Gln Ala Leu Leu Cys
    50                  55                  60

Gln Lys Ala Ile Gly Thr Phe
65                  70
```

CLEANING COMPOSITION

FIELD OF THE INVENTION

The present invention relates to a cleaning composition comprising a surfactant system and a hydrophobin, in particular a class II hydrophobin. The composition provides good and long lasting suds.

BACKGROUND OF THE INVENTION

Cleaning compositions should have a good suds profile while providing good soil and grease cleaning. Users usually see foam as an indicator of the performance of the cleaning composition. Moreover, the user of a cleaning composition may also use the suds profile and the appearance of the foam (density, whiteness) as an indicator that the wash solution still contains active cleaning ingredients. This is particularly the case for manual washing, also referred to herein as hand-washing, where the user usually doses the cleaning composition depending on the suds remaining and renews the wash solution when the suds/foam subsides or when the foam does not look thick enough. Thus, a cleaning composition, particularly a manual wash cleaning composition that generates little or low density foam would tend to be replaced by the user more frequently than is necessary.

Thus, it is desirable for a cleaning composition to provide good foam height and density as well as good foam duration during the initial mixing of the composition with water and during the entire washing operation. When used in a manual-washing process, the composition preferably also provides a pleasant washing experience, i.e, good feel on the user's hands during the wash. Preferably cleaning compositions are also easy to rinse. Preferably in addition, the composition provides a good finish to the washed items.

There is also the desire to reduce the amount of surfactants without impacting suds. Thus, there is the need to find new compositions that improve suds longevity in hand washing.

SUMMARY OF THE INVENTION

According to the first aspect of the invention, there is provided a cleaning composition, preferably in liquid form. The composition comprises a surfactant system and a class II hydrophobin.

The "class II hydrophobin" of the composition of the invention is herein sometimes referred to as "the hydrophobin of the invention".

The "surfactant system" of the composition of the invention is herein sometimes referred to as "the surfactant system of the invention".

Hydrophobin are cystein-rich proteins that are expressed by filamentous fungi. They are known for their ability to form a self-assemble at hydrophobic-hydrophilic interfaces into an amphipathic film. During the course of this work, it has been found that class II hydrophobins improve suds longevity in cleaning compositions comprising the surfactant system of the invention.

The composition provides good grease removal from all types of surfaces. Preferably the composition is a hand dishwashing composition.

The surfactant system of the composition of the invention comprises an anionic surfactant and a primary co-surfactant selected from the group consisting of amphoteric surfactant, zwitteronic surfactant and mixtures thereof. The composition can further comprise a non-ionic surfactant.

The anionic surfactant can be any anionic cleaning surfactant, especially preferred anionic surfactants are selected from the group consisting of alkyl sulfate, alkyl alkoxy sulfate, alkyl benzene sulfonate, paraffin sulfonate and mixtures thereof. Preferred anionic surfactants are selected from alkyl sulfate, alkyl alkoxy sulfate and mixtures thereof, a preferred alkyl alkoxy sulfate is alkyl ethoxy sulfate. Preferred anionic surfactant for use herein is a mixture of alkyl sulfate and alkyl ethoxy sulfate.

Extremely useful surfactant systems for use herein include those comprising anionic surfactants, in combination with amine oxide, especially alkyl dimethyl amine oxides, and/or betaine surfactants.

Preferably, the surfactant system comprises anionic surfactant and amphoteric surfactant, more preferably in a weight ratio of from 2:1 to 4:1. More preferably the anionic surfactant is mixture of alkyl sulfate and alkyl ethoxy sulfate and the amphoteric surfactant is an amine oxide and the anionic surfactant and the amphoteric surfactant are in a weight ratio of from 2:1 to 4:1.

Another preferred surfactant system for use herein is an anionic and amphoteric/zwitterionic system in which the amphoteric to zwitterionic weight ratio is preferably from about 2:1 to about 1:2. In particular a system in which the amphoteric surfactant is an amine oxide surfactant and the zwitteronic surfactant is a betaine and the weight ratio of the amine oxide to the betaine is about 1:1.

Also preferred for use herein are surfactant systems further comprising non-ionic surfactants. Especially preferred nonionic surfactants are alkyl alkoxylated nonionic surfactants, especially alkyl ethoxylated surfactants.

Especially preferred surfactant systems for the composition of the invention comprise an anionic surfactant preferably selected from the group consisting of alkyl sulfate, alkyl alkoxy sulfate and mixtures thereof, and an amphoteric surfactant, preferably an amino oxide surfactant and a non-ionic surfactant. In summary, the most preferred surfactant system for use herein comprises a mixture of alkyl sulfate and alkyl alkoxy sulfate, amine oxide and non-ionic surfactant, especially an alkyl ethoxylated sulfate surfactant, alkyl dimethyl amine oxide and an alkyl ethoxylate nonionic surfactant.

Preferably, the composition of the invention comprises an enzyme. Enzymes can negatively affect suds by facilitating fatty soil removal from substrates and this negative effect can be overcome by the presence of hydrophobins in the composition. Lipase is a preferred enzyme for use herein. Other enzymes suitable enzymes for use herein are selected from the group consisting of proteases, amylases, cellulases and fatty acid transforming enzymes such as oleate hydratase, lipoxygenase and fatty acid decarboxylase and mixtures thereof. Specially preferred are compositions comprising lipases and an enzyme from the group consisting of proteases, amylases, cellulases and fatty acid transforming enzymes such as oleate hydratase, lipoxygenase and fatty acid decarboxylase.

The composition of the invention can further comprise a salt of a divalent cation. In particular, a salt of magnesium. Magnesium cations can work in combination with the hydrophobin and the surfactant system of the invention by strengthening and broadening the grease cleaning profile as well as the longevity of suds of the composition.

The composition of the invention can further comprise a cyclic diamine Cyclic diamines can work in combination with the hydrophobin and the surfactant system of the invention by strengthening and broadening the grease cleaning profile as well as the suds duration of the composition.

The composition of the invention can further comprise a chelant. Chelants can act in combination with the hydrophin of the invention to provide improved grease cleaning. Preferred chelants for use herein are aminophosphonate and aminocarboxylated chelants in particular aminocarboxylated chelants such as MGDA and GLDA.

According to the second aspect of the invention there is provided a method of manually washing dishware using the composition of the invention. The composition of the invention can be used in neat form (direct application). Alternatively, the composition of the invention can also be used in diluted form (full sink). There is also provided the use of the class II hydrophobins in hand dishwashing for suds longevity improvement, especially suds duration improvement in presence of greasy and/or oily soils, in cleaning compositions comprising a surfactant system comprising an anionic surfactant and a primary co-surfactant selected from the group consisting of amphoteric, zwitteronic and mixtures thereof. There is also provided the use of the class II hydrophobins in hand dishwashing for grease emulsification in cleaning compositions comprising a surfactant system comprising an anionic surfactant and a primary co-surfactant selected from the group consisting of amphoteric, zwitterionic and mixtures thereof.

The elements of the composition of the invention described in relation to the first aspect of the invention apply mutatis mutandis to the other aspects of the invention.

DETAILED DESCRIPTION OF THE INVENTION

The present invention envisages a cleaning composition, preferably a hand dishwashing cleaning composition, comprising a specific surfactant system and a class II hydrophobin. The composition of the invention provides very good suds duration especially in presence of fatty and/or oily soils. The invention also envisages a method of hand dishwashing and use of the composition for prolonging suds duration.

Hydrophobins

As described in Wosten, Annu. Rev. Microbiol. 2001, 55, 625646, hydrophobins are proteins generally of fungal origin that play a broad range of roles in the growth and development of filamentous fungi. For example, they are involved in the formation of aerial structures and in the attachment of hyphae to hydrophobic surfaces. The mechanisms by which hydrophobins perform their function are based around their property to self-assemble at hydrophobic-hydrophilic interfaces into an amphipathic film. Typically, hydrophobins are divided into classes I and II. As described in more detail herein, the assembled amphipathic films of class II hydrophobins are capable of re-dissolving in a range of solvents (particularly although not exclusively an aqueous ethanol) at room temperature. In contrast, the assembled amphipathic films of class I hydrophobins are much less soluble, re-dissolving only in strong acids such as trifluoroacetic acid or formic acid. Detergent compositions containing hydrophobins are known in the art. For example, US 2009/0101167 (corresponding to WO 2007/014897) describes the use of hydrophobins, particularly fusion hydrophobins, for washing textiles and washing compositions containing them. US 2014/0031272 describes a cleaning composition comprising a hydrophobin and a lipolytic enzyme for removing lipid-based stains from surfaces.

It has surprisingly been found that cleaning composition comprising class II hydrophobins and the surfactant system of the invention demonstrate long lasting suds despite decreased surfactant levels.

Hydrophobins are polypeptides obtained or obtainable from a microorganism. The microorganism may preferably be a bacteria or a fungus, more preferably a fungus. In this specification the term "hydrophobin" is defined as meaning a polypeptide capable of self-assembly at a hydrophilic/hydrophobic interface, and having the general formula:

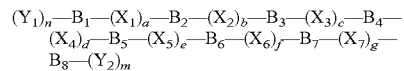

wherein: m and n are independently 0 to 2000; $B_1$, $B_2$, $B_3$, $B_4$, $B_5$, $B_6$, $B_7$ and $B_8$ are each independently amino acids selected from Cys, Leu, Ala, Pro, Ser, Thr, Met or Gly, at least 6 of the residues $B_1$ through $B_8$ being Cys; $X_1$, $X_2$, $X_3$, $X_4$, $X_5$, $X_6$, $X_7$, $Y_1$ and $Y_2$ independently represent any amino acid; a is 1 to 50; b is 0 to 5; c is 1 to 100; d is 1 to 100; e is 1 to 50; f is 0 to 5; and g is 1 to 100.

Class I and II Hydrophobins

In the art, hydrophobins are divided into classes I and II. Class I hydrophobins are outside the scope of current invention. The compositions of the invention comprise class II hydrophobins. It is known in the art that hydrophobins of classes I and II can be distinguished on a number of grounds, both structurally and based on physical parameters including solubility. As described herein, hydrophobins self-assemble at an interface (especially a water/air interface) into amphipathic interfacial films. The assembled amphipathic films of class I hydrophobins are generally re-solubilised only in strong acids (typically those having a pKa of lower than 4, such as formic acid or trifluoroacetic acid), whereas those of class II are soluble in a wider range of solvents.

In one embodiment, the term "class II hydrophobin" means a hydrophobin having the above-described self-assembly property at a water/air interface, the assembled amphipathic films being capable of redissolving to a concentration of at least 0.1% (w/w) in an aqueous ethanol solution (60% v/v) at room temperature. In contrast, in this embodiment, the term "class I hydrophobin" means a hydrophobin having the above-described self-assembly property but which does not have this specified redissolution property.

In another embodiment the term "class II hydrophobin" means a hydrophobin having the above-described self-assembly property at a water/air interface and the assembled amphipathic films being capable of redissolving to a concentration of at least 0.1% (w/w) in an aqueous sodium dodecyl sulphate solution (2% w/w) at room temperature. In contrast, in this embodiment, the term "class I hydrophobin" means a hydrophobin having the above-described self-assembly property but which does not have this specified redissolution property.

Hydrophobins of classes I and II may also be distinguished by the hydrophobicity/hydrophilicity of a number of regions of the hydrophobin protein. The relative hydrophobicity/hydrophilicity of the various regions of the hydrophobin protein can be established by comparing the hydropathy pattern of the hydrophobin using the method set out in Kyte and Doolittle, J. Mol. Biol., 1982, 157, 105-132. According to the teaching of this reference, a computer program can be used to progressively evaluate the hydrophilicity and hydrophobicity of a protein along its amino acid sequence. For this purpose, the method uses a hydropathy scale (based on a number of experimental observations derived from the literature) comparing the hydrophilic and hydrophobic properties of each of the 20 amino acid side-chains. The program uses a moving-segment approach that continuously determines the average hydropathy within a segment of predetermined length as it advances through the sequence. The consecutive scores are plotted from the amino to the carboxy terminus. At the same time, a midpoint line is printed that corresponds to the grand average of the hydropathy of the amino acid compositions found in most of the sequenced proteins. The method is further described for hydrophobins in Wessels, Adv. Microbial Physiol. 1997, 38, 1-45.

The term "class II hydrophobin" means a hydrophobin having the above-described self-assembly property and in which the region between the residues $B_3$ and $B_4$, i.e. the moiety $(X_3)_e$, is predominantly hydrophobic. In contrast, the term "class I hydrophobin" means a hydrophobin having the above-described self-assembly property but in which the region between the residues $B_3$ and $B_4$, i.e. the group $(X_3)_e$, is predominantly hydrophilic. Alternatively the region between the residues $B_7$ and $B_8$, i.e. the moiety $(X_7)_g$, is predominantly hydrophobic for "class II hydrophobin", while being predominantly hydrophilic for "class I hydrophobin".

Structurally class II hydrophobins may also be characterised by their sequences. In one embodiment, the class II hydrophobins used in the present invention have the general formula (I):

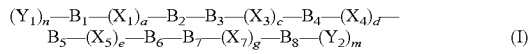

$$(Y_1)_n-B_1-(X_1)_a-B_2-B_3-(X_3)_c-B_4-(X_4)_d-B_5-(X_5)_e-B_6-B_7-(X_7)_g-B_8-(Y_2)_m \qquad (I)$$

wherein: m and n are independently 0 to 200; $B_1$, $B_2$, $B_3$, $B_4$, $B_5$, $B_6$, $B_7$ and $B_8$ are each independently amino acids selected from Cys, Leu, Ala, Ser, Thr, Met or Gly, at least 6 of the residues $B_1$ through $B_8$ being Cys; a is 6 to 12; c is 8 to 16; d is 2 to 20; e is 4 to 12; and g is 5 to 15. $X_1$, $X_3$, $X_4$, $X_5$, $X_7$, $Y_1$ and $Y_2$ independently represent any amino acid.

In the formula (I), m and n are preferably independently 0 to 10.

In the formula (I), a is preferably 7 to 11.

In the formula (I), c is preferably 10 to 12, more preferably 11.

In the formula (I), d is preferably 4 to 18, more preferably 4 to 16.

In the formula (I), e is preferably 6 to 10, more preferably 9 or 10.

In the formula (I), g is preferably 6 to 12, more preferably 7 to 10.

In the formula (I) preferably $B_1$, $B_2$, $B_3$, $B_4$, $B_5$, $B_6$, $B_7$ and $B_8$ are each independently amino acids selected from Cys, Leu or Ser, at least 7, preferably all 8 of the residues $B_1$ through $B_8$ being Cys. When 7 of the residues $B_1$ through $B_8$ are Cys, it is preferred that: (a) $B_1$ and $B_3$ through $B_8$ are Cys and $B_2$ is other than Cys; (b) $B_1$ through $B_7$ are Cys and $B_8$ is other than Cys, (c) $B_1$ is other than Cys and $B_2$ through $B_8$ are Cys. When 7 of the residues $B_1$ through $B_8$ are Cys, it is preferred that the other residue is Ser, Pro or Leu.

In the formulae (I), preferably the group $(X_3)$, comprises the sequence motif ZZXZ, wherein Z is an aliphatic amino acid; and X is any amino acid. In this specification the term "aliphatic amino acid" means an amino acid selected from the group consisting of glycine (G), alanine (A), leucine (L), isoleucine (I), valine (V) and proline (P). More preferably, the group $(X_3)$, comprises the sequence motif selected from the group consisting of LLXV, ILXV, ILXL, VLXL and VLXV. Most preferably, the group $(X_3)$, comprises the sequence motif VLXV.

Alternatively, in the formulae (II), preferably the group $(X_3)$ comprises the sequence motif ZZXZZXZ, wherein Z is an aliphatic amino acid; and X is any amino acid. More preferably, the group $(X_3)$ comprises the sequence motif VLZVZXL, wherein Z is an aliphatic amino acid; and X is any amino acid.

In a preferred embodiment, the hydrophobin is obtained from fungi of the genus *Trichoderma* (particularly *Trichoderma harzianum*, *Trichoderma longibrichiatum*, *Trichoderma asperellum*, *Trichoderma Koningiopsis*, *Trichoderma aggressivum*, *Trichoderma stromaticum* or *Trichoderma reesei*). Other sources of fungal derived hydrophobins include *Cryphonectria parasitica*, *Ophiostoma ulmi*, *Gibberella moniliformis*, and *Magnaporthe griesa*. In a preferred embodiment, the hydrophobin is obtained from fungi of the species *Trichoderma reesei*.

In an especially preferred embodiment, the hydrophobin is the protein "HFBII" (SEQ ID NO: 1; obtainable from *Trichoderma reesei*) or a protein having at least 40%, at least 45%, at least 50%, at least 55%, at least 70%, at least 80%, at least 90% or at least 99% sequence identity with SEQ ID NO:1.

The composition of the invention comprises from about 0.001 to about 5%, preferably from about 0.005 to about 2%, more preferably from about 0.01 to about 1% most preferably from about 0.03 to about 0.5% by weight of the composition.

The Cleaning Composition

The cleaning composition is preferably a hand dishwashing cleaning composition, preferably in liquid form. It typically contains from 30% to 95%, preferably from 40% to 90%, more preferably from 50% to 85% by weight of a liquid carrier in which the other essential and optional components are dissolved, dispersed or suspended. One preferred component of the liquid carrier is water.

Preferably the pH of the composition is from about 6 to about 12, more preferably from about 7 to about 11 and most preferably from about 8 to about 10, as measured at 25° C. and 10% aqueous concentration in distilled water. The pH of the composition can be adjusted using pH modifying ingredients known in the art.

Surfactant System

The cleaning composition comprises from about 1% to about 60%, preferably from about 5% to about 50% more preferably from about 8% to about 40% by weight thereof of a surfactant system. The surfactant system preferably comprises an anionic surfactant, more preferably an anionic surfactant selected from the group consisting of alkyl sulfate, alkyl alkoxy surfate, especially alkyl ethoxy sulfate, alkyl benzene sulfonate, paraffin sulfonate and mixtures thereof. The system also comprises an amphoteric, and/or zwitterionic surfactant and optionally a non-ionic surfactant.

Alkyl sulfates are preferred for use herein, especially alkyl ethoxy sulfates; more preferably a combination of alkyl sulfates and alkyl ethoxy sulfates with a combined average ethoxylation degree of less than 5, preferably less than 3, more preferably less than 2 and more than 0.5 and an average level of branching of from about 5% to about 40%.

The composition of the invention preferably comprises an amphoteric and/or zwitterionic surfactant, preferably the amphoteric surfactant comprises an amine oxide, preferably an alkyl dimethyl amine oxide, and the zwitteronic surfactant comprises a betaine surfactant.

The most preferred surfactant system for the detergent composition of the present invention comprise from 1% to 40%, preferably 6% to 35%, more preferably 8% to 30% weight of the total composition of an anionic surfactant, preferably an alkyl alkoxy sulfate surfactant, more preferably an alkyl ethoxy sulfate, combined with 0.5% to 15%, preferably from 1% to 12%, more preferably from 2% to 10% by weight of the composition of amphoteric and/or zwitterionic surfactant, more preferably an amphoteric and even more preferably an amine oxide surfactant, especially and alkyl dimethyl amine oxide. Preferably the composition further comprises a nonionic surfactant, especially an alcohol alkoxylate in particular and alcohol ethoxylate nonionic surfactant. It has been found that such surfactant system in combination with the hydrophobin of the invention provides excellent suds longevity, grease cleaning and good finish of the washed items. Preferably the composition of the invention comprises a mixture of alkyl sulfate and alkyl ethoxy sulfate and alkyl dimethyl amine oxide in a weight ratio of less than about 8:1, more preferably less than about 5:1, more preferably from about 4:1 to about 2:1.

Anionic Surfactant

Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a C 8-C22 alkyl, or acyl group. Such surfactants are employed in the form of water-soluble salts and the salt-forming cation usually is selected from sodium, potassium, ammonium, magnesium and mono-, di- or tri-C 2-C 3 alkanolammonium, with the sodium, cation being the usual one chosen.

The anionic surfactant can be a single surfactant but usually it is a mixture of anionic surfactants. Preferably the anionic surfactant comprises a sulfate surfactant, more preferably a sulfate surfactant selected from the group consisting of alkyl sulfate, alkyl alkoxy sulfate and mixtures thereof. Preferred alkyl alkoxy sulfates for use herein are alkyl ethoxy sulfates.

Sulfated Anionic Surfactant

Preferably the sulfated anionic surfactant is alkoxylated, more preferably, an alkoxylated branched sulfated anionic surfactant having an alkoxylation degree of from about 0.2 to about 4, even more preferably from about 0.3 to about 3, even more preferably from about 0.4 to about 1.5 and especially from about 0.4 to about 1. Preferably, the alkoxy group is ethoxy. When the sulfated anionic surfactant is a mixture of sulfated anionic surfactants, the alkoxylation degree is the weight average alkoxylation degree of all the components of the mixture (weight average alkoxylation degree). In the weight average alkoxylation degree calculation the weight of sulfated anionic surfactant components not having alkoxylated groups should also be included.

Weight average alkoxylation degree=
(x1*alkoxylation degree of surfactant 1+x2*alkoxylation degree of surfactant 2+ . . . )/(x1+x2+ . . . )

wherein x1, x2, . . . are the weights in grams of each sulfated anionic surfactant of the mixture and alkoxylation degree is the number of alkoxy groups in each sulfated anionic surfactant.

Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the sulfated anionic surfactant used in the detergent of the invention. Most preferably the branched sulfated anionic surfactant is selected from alkyl sulfates, alkyl ethoxy sulfates, and mixtures thereof.

The branched sulfated anionic surfactant can be a single anionic surfactant or a mixture of anionic surfactants. In the case of a single surfactant the percentage of branching refers to the weight percentage of the hydrocarbyl chains that are branched in the original alcohol from which the surfactant is derived.

In the case of a surfactant mixture the percentage of branching is the weight average and it is defined according to the following formula:

Weight average of branching (%)=[(x1*wt % branched alcohol 1 in alcohol 1+x2*wt % branched alcohol 2 in alcohol 2+ . . . )/(x1+x2+ . . . )]*100 wherein x1, x2, . . . are the weight in grams of each alcohol in the total alcohol mixture of the alcohols which were used as starting material for the anionic surfactant for the detergent of the invention. In the weight average branching degree calculation the weight of anionic surfactant components not having branched groups should also be included.

Suitable sulfate surfactants for use herein include water-soluble salts of C8-C18 alkyl or hydroxyalkyl, sulfate and/or ether sulfate. Suitable counterions include alkali metal cation or ammonium or substituted ammonium, but preferably sodium.

The sulfate surfactants may be selected from C8-C18 primary, branched chain and random alkyl sulfates (AS); C8-C18 secondary (2,3) alkyl sulfates; C8-C18 alkyl alkoxy sulfates (AExS) wherein preferably x is from 1-30 in which the alkoxy group could be selected from ethoxy, propoxy, butoxy or even higher alkoxy groups and mixtures thereof.

Alkyl sulfates and alkyl alkoxy sulfates are commercially available with a variety of chain lengths, ethoxylation and branching degrees. Commercially available sulfates include, those based on Neodol alcohols ex the Shell company, Lial—Isalchem and Safol ex the Sasol company, natural alcohols ex The Procter & Gamble Chemicals company.

Preferably, the anionic surfactant comprises at least 50%, more preferably at least 60% and especially at least 70% of a sulfate surfactant by weight of the anionic surfactant. Especially preferred detergents from a cleaning view point are those in which the anionic surfactant comprises more than 50%, more preferably at least 60% and especially at least 70% by weight thereof of sulfate surfactant and the sulfate surfactant is selected from the group consisting of alkyl sulfates, alkyl ethoxy sulfates and mixtures thereof. Even more preferred are those in which the anionic surfactant is an alkyl ethoxy sulfate with a degree of ethoxylation of from about 0.2 to about 3, more preferably from about 0.3 to about 2, even more preferably from about 0.4 to about 1.5, and especially from about 0.4 to about 1. They are also preferred anionic surfactant having a level of branching of from about 5% to about 40%, even more preferably from about 10% to 35% and especially from about 20% to 30%.

Sulphonate Surfactant

Suitable sulphonate surfactants for use herein include water-soluble salts of C8-C18 alkyl or hydroxyalkyl sulphonates; C11-C18 alkyl benzene sulphonates (LAS), modified alkylbenzene sulphonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulphonate (MES); and alpha-olefin sulphonate (AOS). Those also include the paraffin sulphonates may be monosulphonates and/or disulphonates, obtained by sulphonating paraffins of 10 to 20 carbon atoms. The sulfonate surfactant also include the alkyl glyceryl sulphonate surfactants.

Non Ionic Surfactant

Nonionic surfactant, when present, is comprised in a typical amount of from 0.1% to 40%, preferably 0.2% to 20%, most preferably 0.5% to 10% by weight of the composition. Suitable nonionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred nonionic surfactants are the condensation products of guerbet alcohols with from 2 to 18 moles, preferably 2 to 15, more preferably 5-12 of ethylene oxide per mole of alcohol.

Other suitable non-ionic surfactants for use herein include fatty alcohol polyglycol ethers, alkylpolyglucosides and fatty acid glucamides.

Amphoteric Surfactant

Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3) O wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides. Preferred amine oxides include linear C10, linear C10-C12, and linear C12-C14 alkyl dimethyl amine oxides. As used herein "mid-branched" means that the amine oxide has one alkyl moiety having n1 carbon atoms with one alkyl branch on the alkyl moiety having n2 carbon atoms. The alkyl branch is located on the a carbon from the nitrogen on the alkyl moiety. This type of branching for the amine oxide is also known in the art as an internal amine oxide. The total sum of n1 and n2 is from 10 to 24 carbon atoms, preferably from 12 to 20, and more preferably from 10 to 16. The number of carbon atoms for the one alkyl moiety (n1) should be approximately the same number of carbon atoms as the one alkyl branch (n2) such that the one alkyl moiety and the one alkyl branch are symmetric. As used herein "symmetric" means that |n1-n2| is less than or equal to 5, preferably 4, most preferably from 0 to 4 carbon atoms in at least 50 wt %, more preferably at least 75 wt % to 100 wt % of the mid-branched amine oxides for use herein.

The amine oxide further comprises two moieties, independently selected from a C1-3 alkyl, a C1-3 hydroxyalkyl group, or a polyethylene oxide group containing an average of from about 1 to about 3 ethylene oxide groups. Preferably the two moieties are selected from a C1-3 alkyl, more preferably both are selected as a C1 alkyl.

Zwitterionic Surfactant

Other suitable surfactants include betaines, such as alkyl betaines, alkylamidobetaine, amidazoliniumbetaine, sulfobetaine (INCI Sultaines) as well as the Phosphobetaine and preferably meets formula (I):

R1-[CO—X(CH2)*n*]*x*-N+(R2)(R3)-(CH2)*m*-[CH(OH)—CH2]*y*-Y— (I) 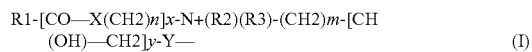

wherein

R1 is a saturated or unsaturated C6-22 alkyl residue, preferably C8-18 alkyl residue, in particular a saturated C10-16 alkyl residue, for example a saturated C12-14 alkyl residue;

X is NH, NR4 with C1-4 Alkyl residue R4, O or S, n a number from 1 to 10, preferably 2 to 5, in particular 3, x 0 or 1, preferably 1, R2, R3 are independently a C1-4 alkyl residue, potentially hydroxy substituted such as a hydroxyethyl, preferably a methyl.

m a number from 1 to 4, in particular 1, 2 or 3, y 0 or 1 and

Y is COO, SO3, OPO(OR5)O or P(O)(OR5)O, whereby R5 is a hydrogen atom H or a C1-4 alkyl residue.

Preferred betaines are the alkyl betaines of the formula (Ia), the alkyl amido propyl betaine of the formula (Ib), the Sulfo betaines of the formula (Ic) and the Amido sulfobetaine of the formula (Id);

R1-N+(CH3)2-CH2COO— (Ia) 

R1-CO—NH(CH2)3-N+(CH3)2-CH2COO— (Ib) 

R1-N+(CH3)2-CH2CH(OH)CH2SO3- (Ic) 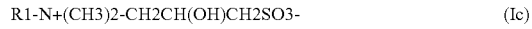

R1-CO—NH—(CH2)3-N+(CH3)2-CH2CH(OH)CH2SO3- (Id) 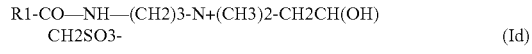

in which R11 as the same meaning as in formula I. Particularly preferred betaines are the Carbobetaine [wherein Y—=COO—], in particular the Carbobetaine of the formula (Ia) and (Ib), more preferred are the Alkylamidobetaine of the formula (Ib).

Examples of suitable betaines and sulfobetaine are the following [designated in accordance with INCI]: Almondamidopropyl of betaines, Apricotam idopropyl betaines, Avocadamidopropyl of betaines, Babassuamidopropyl of betaines, Behenam idopropyl betaines, Behenyl of betaines, betaines, Canolam idopropyl betaines, Capryl/Capram idopropyl betaines, Carnitine, Cetyl of betaines, Cocamidoethyl of betaines, Cocam idopropyl betaines, Cocam idopropyl Hydroxysultaine, Coco betaines, Coco Hydroxysultaine, Coco/Oleam idopropyl betaines, Coco Sultaine, Decyl of betaines, Dihydroxyethyl Oleyl Glycinate, Dihydroxyethyl Soy Glycinate, Dihydroxyethyl Stearyl Glycinate, Dihydroxyethyl Tallow Glycinate, Dimethicone Propyl of PG-betaines, Erucam idopropyl Hydroxysultaine, Hydrogenated Tallow of betaines, Isostearam idopropyl betaines, Lauram idopropyl betaines, Lauryl of betaines, Lauryl Hydroxysultaine, Lauryl Sultaine, Milkam idopropyl betaines, Minkamidopropyl of betaines, Myristam idopropyl betaines, Myristyl of betaines, Oleam idopropyl betaines, Oleam idopropyl Hydroxysultaine, Oleyl of betaines, Olivamidopropyl of betaines, Palmam idopropyl betaines, Palm itam idopropyl betaines, Palmitoyl Carnitine, Palm Kernelam idopropyl betaines, Polytetrafluoroethylene Acetoxypropyl of betaines, Ricinoleam idopropyl betaines, Sesam idopropyl betaines, Soyam idopropyl betaines, Stearam idopropyl betaines, Stearyl of betaines, Tallowam idopropyl betaines, Tallowam idopropyl Hydroxysultaine, Tallow of betaines, Tallow Dihydroxyethyl of betaines, Undecylenam idopropyl betaines and Wheat Germam idopropyl betaines.

A preferred betaine is, for example, Cocoamidopropylbetaine.

Enzymes

The composition of the invention preferably comprises one or more enzyme such as protease, lipase, cutinase, amylase, carbohydrase, cellulase, pectinase, mannanase, arabinase, galactanase, xylanase, perhydrolase, oxidase, e.g., laccase, lipoxygenase, oleate hydratase, fatty acid decarboxylase, and/or peroxidase. Preferred herein are compositions comprising an enzyme selected from the group consisting of lipase, protease, amylase, cellulase, lipoxygenase, oleate hydratase and/or fatty acid decarboxylase. Most preferred herein are compositions comprising lipase.

A preferred combination of enzymes comprises, e.g., a protease, lipase and amylase. When present in a composition, the aforementioned enzymes may be present at levels from 0.00001 to 2%, from 0.0001 to 1% or from 0.001 to 0.5% enzyme protein by weight of the composition.

Cyclic Diamine

The composition of the invention preferably comprises from about 0.1% to about 10%, more preferably from about 0.2% to about 5%, and especially from about 0.3% to about 2%, by weight of the composition of a cyclic diamine. The preferred cyclic diamine for use herein is:

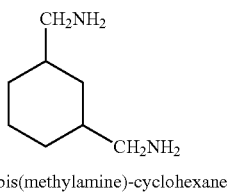

1, 3-bis(methylamine)-cyclohexane

Divalent Cation

When utilized in the composition of the invention, divalent cations such as calcium and magnesium ions, preferably magnesium ions, are preferably added as a hydroxide, chloride, acetate, sulfate, formate, oxide, lactate or nitrate salt to the compositions of the present invention, typically at an active level of from 0.01% to 1.5%, preferably from 0.015% to 1%, more preferably from 0.025% to 0.5%, by weight of the composition.

Chelant

The composition herein may optionally further comprise a chelant at a level of from 0.1% to 20%, preferably from 0.2% to 5%, more preferably from 0.2% to 3% by weight of the composition.

As commonly understood in the detergent field, chelation herein means the binding or complexation of a bi- or multi-dentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale, or destabilizing soils facilitating their removal accordingly. The ligand forms a chelate complex with the substrate. The term is reserved for complexes in which the metal ion is bound to two or more atoms of the chelant.

Suitable chelating agents can be selected from the group consisting of amino carboxylates, amino phosphonates, polyfunctionally-substituted aromatic chelating agents and mixtures thereof.

Amino carboxylates include ethylenediaminetetra-acetates, N-hydroxyethylethylenediaminetriacetates, nitrilotriacetates, ethylenediamine tetraprorionates, triethylenetetraaminehexacetates, diethylenetriaminepentaacetates, and ethanoldiglycines, alkali metal, ammonium, and substituted ammonium salts therein and mixtures therein, as well as MGDA (methyl-glycine-diacetic acid), and salts and derivatives thereof and GLDA (glutamic-N,N-diacetic acid) and salts and derivatives thereof. GLDA (salts and derivatives thereof) is especially preferred according to the invention, with the tetrasodium salt thereof being especially preferred.

Other suitable chelants include amino acid based compound or a succinate based compound. The term "succinate based compound" and "succinic acid based compound" are used interchangeably herein. Other suitable chelants are described in U.S. Pat. No. 6,426,229. Particular suitable chelants include; for example, aspartic acid-N-monoacetic acid (ASMA), aspartic acid-N,N-diacetic acid (ASDA), aspartic acid-N-monopropionic acid (ASMP), iminodisuccinic acid (IDS), Imino diacetic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), alanine-N,N-diacetic acid (ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof. Also suitable is ethylenediamine disuccinate ("EDDS"), especially the [S,S] isomer as described in U.S. Pat. No. 4,704,233. Furthermore, Hydroxyethyleneiminodiacetic acid, Hydroxyiminodisuccinic acid, Hydroxyethylene diaminetriacetic acid are also suitable.

Other chelants include homopolymers and copolymers of polycarboxylic acids and their partially or completely neutralized salts, monomeric polycarboxylic acids and hydroxycarboxylic acids and their salts. Preferred salts of the above-mentioned compounds are the ammonium and/or alkali metal salts, i.e. the lithium, sodium, and potassium salts, and particularly preferred salts are the sodium salts.

Suitable polycarboxylic acids are acyclic, alicyclic, heterocyclic and aromatic carboxylic acids, in which case they contain at least two carboxyl groups which are in each case separated from one another by, preferably, no more than two carbon atoms. Polycarboxylates which comprise two carboxyl groups include, for example, water-soluble salts of, malonic acid, (ethylenedioxy) diacetic acid, maleic acid, diglycolic acid, tartaric acid, tartronic acid and fumaric acid. Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. Preferred are the polycarboxylates end capped with sulfonates.

Amino phosphonates are also suitable for use as chelating agents and include ethylenediaminetetrakis (methylenephosphonates) as DEQUEST. Preferred are these amino phosphonates that do not contain alkyl or alkenyl groups with more than about 6 carbon atoms. Polyfunctionally-substituted aromatic chelating agents are also useful in the compositions herein such as described in U.S. Pat. No. 3,812,044. Preferred compounds of this type are dihydroxydisulfobenzenes such as 1,2-dihydroxy-3,5-disulfobenzene.

Further suitable polycarboxylates chelants for use herein include citric acid, lactic acid, acetic acid, succinic acid, formic acid; all preferably in the form of a water-soluble salt. Other suitable polycarboxylates are oxodisuccinates, carboxymethyloxysuccinate and mixtures of tartrate monosuccinic and tartrate disuccinic acid such as described in U.S. Pat. No. 4,663,071.

The most preferred chelants for use in the present invention are selected from the group consisting of diethylenetetraamine pentaacetic acid (DTPA), MGDA, GLDA, citrate and mixtures thereof.

The composition herein may comprise a number of optional ingredients such as preservatives, conditioning polymers, cleaning polymers, surface modifying polymers, soil flocculating polymers, structurants, emollients, humectants, skin rejuvenating actives, carboxylic acids, scrubbing particles, bleach and bleach activators, perfumes, malodor control agents, pigments, dyes, opacifiers, beads, pearlescent particles, microcapsules, antibacterial agents, pH adjusters, buffering means, water or any other dilutents or solvents compatible with the composition.

Method of Washing

The second aspect of the invention is directed to a method of washing dishware with the composition of the present invention. Said method comprises the step of applying the composition, preferably in liquid form, onto the dishware surface, either directly or by means of a cleaning implement, i.e., in neat form.

By "in its neat form", it is meant herein that said composition is not diluted in a full sink of water. The composition is applied directly onto the surface to be treated and/or onto a cleaning device or implement such as a dish cloth, a sponge or a dish brush without undergoing major dilution (immediately) prior to the application. The cleaning device or implement is preferably wet before or after the composition is delivered to it. In the method of the invention, the composition can also be applied in diluted form. Both neat and dilute application give rise to good and long lasting suds in the presence in fat and/or oily soils, even when the level of surfactant used is lower than in conventional compositions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

Test Protocol

A test solution is prepared by subsequently adding 10 ml of detergent test product, 0.22 ml of olive oil and 1 ml of Hydrophobin solution to a 40 ml glass vial (dimensions: 95*27.5 mm—ex VWR—code 548-0156). For nil hydrophobin test solutions 1 ml of demineralised water is added. For nil detergent test legs 10 ml of 15 gpg water is added.

The test solution is mixed in the closed test vial by stirring the solution at room temperature for 2 minutes on a magnetic stirring plate (AM4 Multiple Heating Magnetic Stirrer plate ex Velp Scientifica—stirring position 4) using a magnetic stirrer of 1 cm by 3 mm, followed by manually shaking the sample for 20 seconds in an upwards downwards direction (2 up and down cycles per second, +/−30 cm up and 30 cm down).

The test solution is consequently stirred as above for 1 hour, this time the closed test vial being immersed in a glass beaker comprising water at a constant temperature of 35 degrees C. The sample is consequently shaken for another 20 seconds as above. A picture is taken 5 seconds after end of shaking and the foam height is measured with a ruler.

Test Results

It can be clearly seen from the data in the table below that example formulations comprising a mixed anionic surfactant cosurfactant system with a class II hydrophobin have a superior foam profile compared to comparative examples solely comprising class II hydrophobin nil detergent (comparative examples 1 and 2), nil hydrophobin formulations (comparative example 3), solely comprising anionic surfactant and class II hydrophobin nil cosurfactant (comparative example 4 and 5) or comparative examples 6 and 7 comprising class I hydrophobins.

|  | Detergent Test Product | Hydrophobin | Foam height |
|---|---|---|---|
| Example 1 | Mixed AES/AO detergent | HFB II (kappa grade) | 0.6 cm |
| Example 2 | Mixed AES/AO detergent | HFB II (alpha grade) | 0.7 cm |
| Comparative Example 1 | Nil detergent | HFB II (kappa grade) | 0 cm |
| Comparative Example 2 | Nil detergent | HFB II (alpha grade) | 0 cm |
| Comparative Example 3 | Mixed AES/AO detergent | nil | 0.1 cm |
| Comparative Example 4 | SDS detergent | HFB II (kappa grade) | 0 cm |
| Comparative Example 5 | SDS detergent | HFB II (alpha grade) | 0 cm |
| Comparative Example 6 | Mixed AES/AO detergent | HFB I (H*A) | 0.3 cm |
| Comparative Example 7 | Mixed AES/AO detergent | HFB I (H*B) | 0.2 cm |

Test Materials

Detergent Test Products

Mixed AES/AO detergent: Fairy Dark Green, as commercially available in the UK in December 2015, is diluted to half the concentration with demi water and pH is re-trimmed with NaOH till pH 9 (measured as a 10% product concentration in demineralized water at room temperature). This product is then further diluted in 15 gpg water till a total product concentration of 0.12%, comprising an AES/AO concentration of 170 ppm (AES:AO-wt % ratio of 3:1).

AES=C1213 AE0.6S

AO=C1214 dimethyl amine oxide

SDS detergent: A 14% SDS aqueous detergent composition further comprising 0.4% NaCl, 0.6% PPG and 1.2% ethanol, trimmed with NaOH till pH 9 (10% product concentration in demineralized water) is prepared by mixing of individual ingredients. The resulting detergent is diluted in 15 gpg water till a total SDS concentration of 170 ppm.

SDS=sodium dodecyl sulphate (Acmepon SLS 95% USP Kosher grade)—from Sigma Aldrich Olive Oil: Bertoli (Olio Extra Vergine Di Oliva—Originale), as commercially available in Belgium in March 2016.

Hydrophobin test solutions:

Hydrophobin Class I: ex BASF (Germany)
 H Star Protein A Granules
  HFB test solution: 1.8 mg dissolved in 1 ml of demineralized water
 H Star Protein B Granules
  HFB test solution: 2.2 mg dissolved in 1 ml of demineralized water Hydrophobin Class II: ex KU Leuven (Belgium)
 Hydrophobin HFB II (Kappa grade), extracted from *Trichoderma Reesei* (MUCL 44908) in 35%-50% acetonitrile in water solution
  HFB test solution: 1 mL of hydrophobin II (kappa grade) solution. →2.7 ppm active protein in test solution (i.e. detergent test product+oil+hydrophobin solution)
 Hydrophobin HFB II (alpha grade), foam fractionated extract from *Trichoderma Reesei* (MUCL 44908) in 25% ethanol in water solution
  HFB test solution: 1 mL of hydrophobin II (alpha grade) solution. →5.4 ppm active protein in test solution (i.e. detergent test product+oil+hydrophobin solution)

3. A composition according to claim 1 wherein the hydrophobin self-assembles at water/air interface into an amphipathic interfacial film and the assembled amphipathic film re-dissolves to a concentration of at least 0.1% (w/w) in an aqueous sodium dodecyl sulphate solution (2% w/w) at room temperature.

4. A composition according to claim 1 wherein the hydrophobin has the formula:

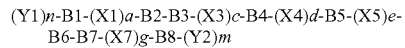

wherein: m and n are independently 0 to 200; B1, B2, B3, B4, B5, B6, B7 and B8 are each independently amino acids selected from Cys, Leu, Ala, Ser, Thr, Met or Gly, at least 6 of the residues B1 through B8 being Cys; a is 6 to 12; c is 8 to 16; d is 2 to 20; e is 4 to 12; and g is 5 to 15; X1, X3, X4, X5, X7, Y1 and Y2 independently represent any amino acid.

5. A composition according to claim 1 wherein the hydrophobin has the formula:

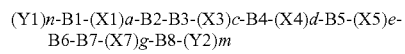

wherein: m and n are independently 0 to 10; B1, B2, B3, B4, B5, B6, B7 and B8 are each independently amino acids selected from Cys, Leu, Ala, Ser, Thr, Met or Gly, at least 6 of the residues B1 through B8 being Cys; a is 7 to 11; c is 10 to 12; d is 4 to 18; e is 6 to 10; and

What is claimed is:

1. A cleaning composition comprising:
   a) from about 1% to about 60% by weight of the composition of a surfactant system comprising from 6% to 35% of an anionic surfactant which is an alkyl alkoxy sulphate, and 0.5% to 15% of a primary co-surfactant which is an amphoteric amine oxide; and
   b) from about 0.001% to about 5% by weight of the composition of a class II hydrophobin.

2. A composition according to claim 1 wherein the hydrophobin self-assembles at water/air interface into an amphipathic interfacial film and the assembled amphipathic film re-dissolves to a concentration of at least 0.1% (w/w) in an aqueous ethanol solution (60% v/v) at room temperature.

g is 6 to 12; X1, X3, X4, X5, X7, Y1 and Y2 independently represent any amino acid.

6. A composition according to claim 1 wherein the hydrophobin has the formula:

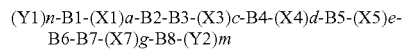

wherein: m and n are independently 0 to 200; B1, B2, B3, B4, B5, B6, B7 and B8 wherein:
 B1 and B3 through B8 are Cys and B2 is other than Cys; or
 B1 through B7 are Cys and B8 is other than Cys; or
 B1 is other than Cys and B2 through B8 are Cys; and
 the residues B1 through B8 that are not Cys are selected from Ser, Pro and Leu and wherein a is 6 to 12; c is 8 to 16; d is 2 to 20; e is 4 to 12; and g is 5 to 15; X1, X3, X4, X5, X7, Y1 and Y2 independently represent any amino acid.

7. A composition according to claim 1 wherein the hydrophobin is obtained from fungi of the genus *Trichoderma*.

8. A composition according to claim 1 wherein the hydrophobin has at least 40% identity with SEQ ID NO:1.

9. A composition according to claim 1 wherein the composition is a hand dishwashing cleaning composition.

10. A composition according to claim 1 wherein the anionic surfactant is a mixture of alkyl sulfate and alkyl alkoxy sulfate and wherein the alkyl alkoxy sulfate is an alkyl ethoxy sulfate.

11. A composition according to claim 1 wherein the anionic surfactant is a mixture of alkyl sulfate and alkyl alkoxy sulfate and the amphoteric surfactant is an alkyl dimethyl amine oxide and wherein the anionic surfactant and amphoteric surfactant are in a weight ratio of from about 4:1 to about 2:1.

12. A composition according to claim 1 wherein the composition further comprises a non-ionic surfactant.

13. A composition according to claim 1 wherein the composition further comprises an enzyme selected from the group consisting of lipase, protease, amylase, cellulase, oleate hydratase, fatty acid lipoxigenase, fatty acid decarboxylase, and mixtures thereof.

14. A composition according to claim 1 wherein the composition further comprises a salt of a divalent cation.

15. A composition according to claim 1 wherein the composition further comprises a cyclic diamine.

16. A composition according to claim 1 wherein the composition further comprises an aminocarboxylate chelant.

17. A method of manually washing dishware comprising the step of delivering a composition according to claim 1 to the dishware in neat or diluted form.

* * * * *